US009872993B2

(12) United States Patent
Zimmerling

(10) Patent No.: US 9,872,993 B2
(45) Date of Patent: Jan. 23, 2018

(54) MRI-SAFE IMPLANT MAGNET WITH ANGULAR MAGNETIZATION

(71) Applicant: MED-EL Elektromedizinische Geraete GmbH, Innsbruck (AT)

(72) Inventor: Martin Zimmerling, Patsch (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 812 days.

(21) Appl. No.: 13/932,315

(22) Filed: Jul. 1, 2013

(65) Prior Publication Data

US 2014/0012349 A1 Jan. 9, 2014

Related U.S. Application Data

(60) Provisional application No. 61/667,474, filed on Jul. 3, 2012.

(51) Int. Cl.
*A61N 1/372* (2006.01)
*A61N 1/36* (2006.01)
*A61N 1/37* (2006.01)

(52) U.S. Cl.
CPC ....... *A61N 1/37229* (2013.01); *A61N 1/3718* (2013.01); *A61N 1/36036* (2017.08)

(58) Field of Classification Search
CPC .............. A61N 1/36036; A61N 1/3718; A61N 1/37229
USPC ............................................ 607/57, 60, 137
See application file for complete search history.

(56) References Cited

U.S. PATENT DOCUMENTS

| 5,196,710 | A | * | 3/1993 | Kalfaian | 250/492.1 |
|---|---|---|---|---|---|
| 6,138,681 | A | * | 10/2000 | Chen et al. | 128/899 |
| 6,991,594 | B2 | * | 1/2006 | Holcomb | 600/9 |
| 7,225,028 | B2 | * | 5/2007 | Della Santina et al. | 607/57 |
| 7,610,096 | B2 | * | 10/2009 | McDonald, III | 607/48 |
| 7,647,120 | B2 | * | 1/2010 | Della Santina et al. | 607/57 |
| 7,991,477 | B2 | * | 8/2011 | McDonald, III | 607/48 |
| 8,260,435 | B2 | * | 9/2012 | Johnson et al. | 607/116 |
| 8,585,569 | B2 | * | 11/2013 | Holcomb | 600/12 |
| 8,634,909 | B2 | * | 1/2014 | Zimmerling et al. | 607/3 |
| 8,652,071 | B2 | * | 2/2014 | Williams | 600/595 |
| 8,670,841 | B2 | * | 3/2014 | Dabney et al. | 607/116 |
| 8,676,325 | B2 | * | 3/2014 | Lindenthaler et al. | 607/42 |
| 2001/0021805 | A1 | * | 9/2001 | Blume et al. | 600/407 |
| 2007/0208403 | A1 | * | 9/2007 | Della Santina et al. | 607/137 |
| 2009/0069869 | A1 | * | 3/2009 | Stouffer et al. | 607/61 |
| 2011/0004278 | A1 | * | 1/2011 | Aghassian et al. | 607/61 |
| 2012/0022616 | A1 | * | 1/2012 | Garnham et al. | 607/60 |
| 2013/0345646 | A1 | * | 12/2013 | Bertrand et al. | 604/248 |
| 2014/0005750 | A1 | * | 1/2014 | Garnham et al. | 607/60 |
| 2014/0012349 | A1 | * | 1/2014 | Zimmerling | 607/57 |

* cited by examiner

*Primary Examiner* — Christopher A Flory
(74) *Attorney, Agent, or Firm* — Sunstein Kann Murphy & Timbers LLP

(57) ABSTRACT

A magnetic arrangement is described for an implantable system for a recipient patient. An implantable coil housing contains a signal coil for transcutaneous communication of an implant communication signal. Freely rotatable within the coil housing is a cylindrical implant magnet for transcutaneous magnetic interaction with a corresponding external attachment magnet. The implant magnet has a central cylinder axis of symmetry, and a magnetization direction along a magnetic axis angled away from the axis of symmetry at a non-zero angle less than 45 degrees.

8 Claims, 4 Drawing Sheets

MRI-SAFE IMPLANT MAGNET WITH ANGULAR MAGNETIZATION

This application claims priority from U.S. Provisional Patent Application 61/667,474, filed Jul. 3, 2012, which is incorporated herein by reference.

FIELD OF THE INVENTION

The present invention relates to implantable medical devices, and specifically, to magnetic elements in such devices that allow for magnetic resonance imaging.

BACKGROUND ART

Some hearing implants such as Middle Ear Implants (MEI's) and Cochlear Implants (CI's) employ attachment magnets in the implantable part and an external part to hold the external part magnetically in place over the implant. For example, as shown in FIG. 1, a typical cochlear implant system may include an external transmitter housing 101 containing transmitting coils 102 and an external attachment magnet 103. The external attachment magnet 103 has a conventional cylindrical disk-shape and a north-south magnetic dipole having an axis that is perpendicular to the skin of the patient to produce external magnetic field lines 104 as shown. Implanted under the patient's skin is a corresponding receiver assembly 105 having similar receiving coils 106 and an implant magnet 107. The implant magnet 107 also has a cylindrical disk-shape and a north-south magnetic dipole having a magnetic axis that is perpendicular to the skin of the patient to produce internal magnetic field lines 108 as shown. The internal receiver housing 105 is surgically implanted and fixed in place within the patient's body. The external transmitter housing 101 is placed in proper position over the skin covering the internal receiver assembly 105 and held in place by interaction between the internal magnetic field lines 108 and the external magnetic field lines 104. Rf signals from the transmitter coils 102 couple data and/or power to the receiving coil 106 which is in communication with an implanted processor module (not shown).

One problem arises when the patient undergoes Magnetic Resonance Imaging (MRI) examination. Interactions occur between the implant magnet and the applied external magnetic field for the MRI. As shown in FIG. 2, the direction magnetization $\overline{m}$ of the implant magnet 202 is essentially perpendicular to the skin of the patient. Thus, the external magnetic field $\overline{B}$ from the MRI may create a torque T on the internal magnet 202, which may displace the internal magnet 202 or the whole implant housing 201 out of proper position. Among other things, this may damage the adjacent tissue in the patient. In addition, the external magnetic field $\overline{B}$ from the MRI may reduce or remove the magnetization $\overline{m}$ of the implant magnet 202 so that it may no longer be strong enough to hold the external transmitter housing in proper position. The implant magnet 202 may also cause imaging artifacts in the MRI image, there may be induced voltages in the receiving coil, and hearing artifacts due to the interaction of the external magnetic field $\overline{B}$ of the MRI with the implanted device. This is especially an issue with MRI field strengths exceeding 1.5 Tesla.

Thus, for existing implant systems with magnet arrangements, it is common to either not permit MRI or at most limit use of MRI to lower field strengths. Other existing solutions include use of a surgically removable magnets, spherical implant magnets (e.g. U.S. Pat. No. 7,566,296), and various ring magnet designs (e.g., U.S. Provisional Patent 61/227, 632, filed Jul. 22, 2009). Among those solutions that do not require surgery to remove the magnet, the spherical magnet design may be the most convenient and safest option for MRI removal even at very high field strengths. But the spherical magnet arrangement requires a relatively large magnet much larger than the thickness of the other components of the implant, thereby increasing the volume occupied by the implant. This in turn can create its own problems. For example, some systems, such as cochlear implants, are implanted between the skin and underlying bone. The "spherical bump" of the magnet housing therefore requires preparing a recess into the underlying bone. This is an additional step during implantation in such applications which can be very challenging or even impossible in case of very young children.

U.S. Patent Publication 20110264172 described an implant magnet having a magnetic dipole with a magnetic axis that is perpendicular to the central cylindrical axis of symmetry of a disk shaped implant magnet—that is, perpendicular to the conventional magnetic axis of a disk-shaped implant magnet. But among other things, such an arrangement requires a significantly greater size implant magnet to achieve the required amount of magnetic attraction with the external attachment magnet.

SUMMARY OF THE INVENTION

Embodiments of the present invention are directed to a magnetic arrangement for an implantable system for a recipient patient. An implantable coil housing contains a signal coil for transcutaneous communication of an implant communication signal. Freely rotatable within the coil housing is a cylindrical implant magnet for transcutaneous magnetic interaction with a corresponding external attachment magnet. The implant magnet has a central cylinder axis of symmetry, and a magnetization direction along a magnetic axis angled away from the axis of symmetry at a non-zero angle less than 45 degrees.

In further specific embodiments, the magnetic axis may be angled away from the axis of symmetry at an angle of more than 10 degrees and less than 30 degrees, e.g., at an angle of 20 degrees. And there may be a lubrication coating covering at least a portion of the implant magnet and reducing rotational friction between the implant magnet and the coil housing.

In any of the above, the implantable system may be a cochlear implant system, a middle ear implant system, a vestibular implant system, or a laryngeal pacemaker implant system.

DETAILED DESCRIPTION OF SPECIFIC EMBODIMENTS

Various embodiments of the present invention are directed to a magnetic arrangement for an implantable system for a recipient patient which is compatible with MRI systems. Unlike a conventional implant magnet that has a magnetization direction along its axis of symmetry (resulting in magnetic poles on each of the circular disk surfaces), and in contrast with the design described in U.S. Patent Publication 20110264172 where the implant magnet has a magnetization direction perpendicular to its axis of symmetry, the implant magnet described herein has an angular or slanted magnetization direction along a magnetic axis that angled away from the axis of symmetry at a limited angle.

Figure 1:
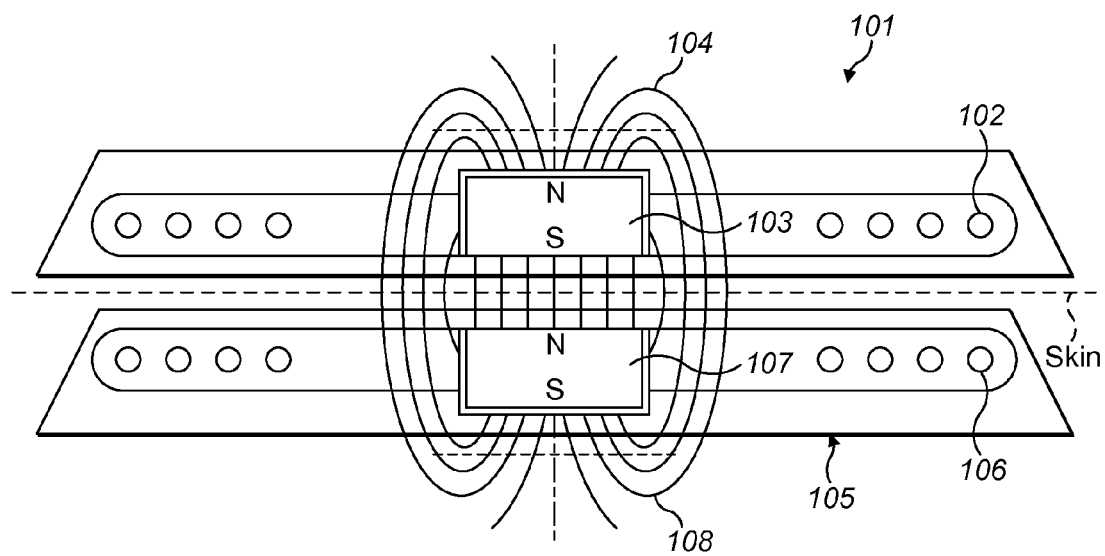
FIG. 1 shows portions of a typical cochlear implant system.
Figure 2:
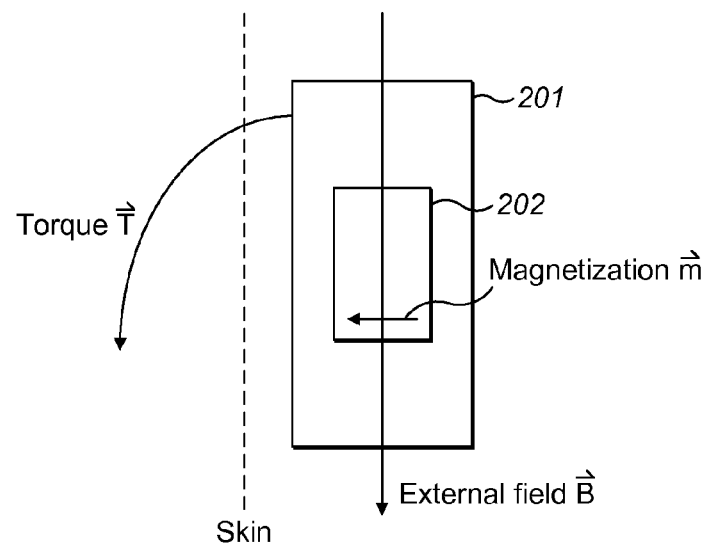
FIG. 2 illustrates the interactions that can occur between an implant magnet and the applied external magnetic field for an MRI system.
Figure 3:
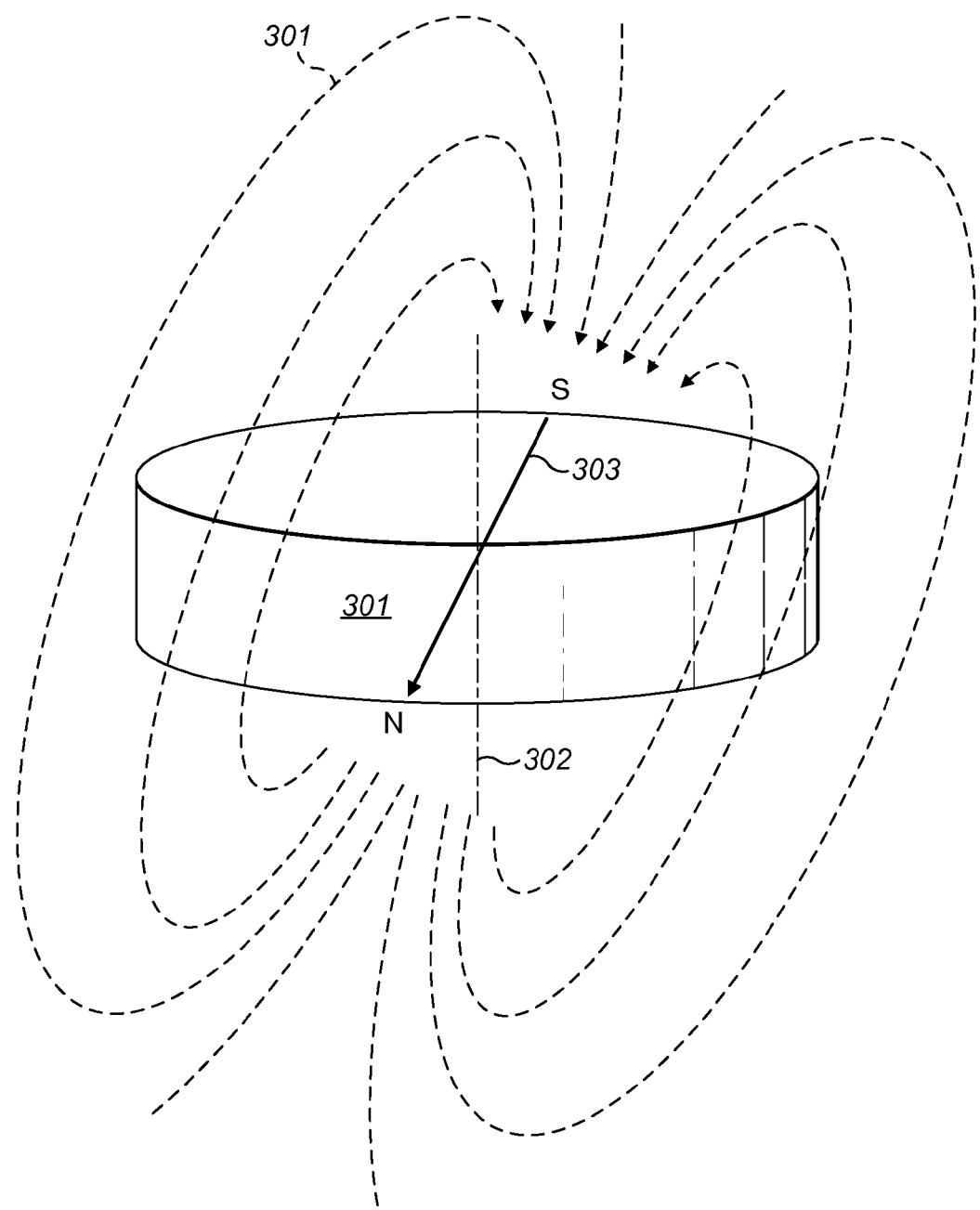
FIG. 3 shows a cylindrical implant magnet having an angular magnetization direction according to an embodiment of the present invention.

FIG. 3 shows a cylindrical implant magnet 300 having a magnetic field 301 an angular magnetization direction 303 according to an embodiment of the present invention. The angular magnetization direction 303 (that is, the magnetic dipole orientation) is at a slanted angle to the center cylinder axis of symmetry 302 which is less than 45°. Typically the angular magnetization direction 303 would be at least 10° and not more than about 30°, for example, around 20°.

Figure 4:
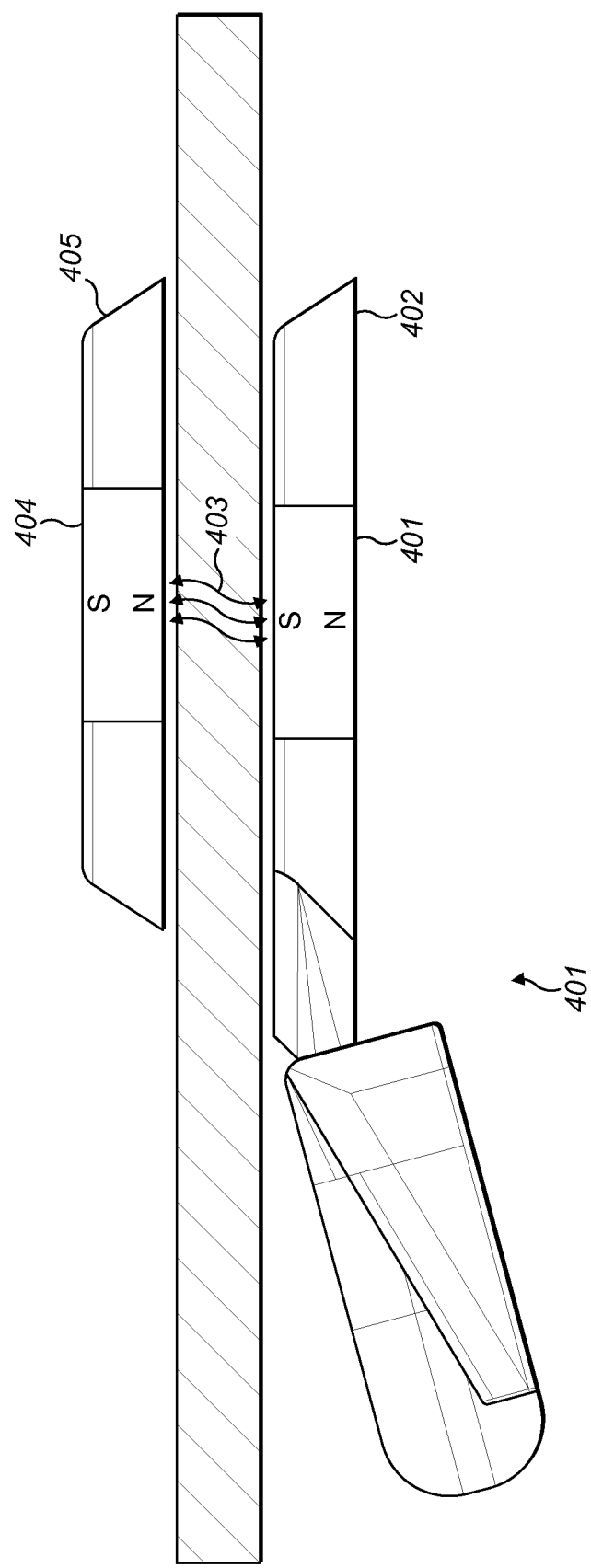
FIG. 4 shows an example of a cochlear implant device having a coil housing and angularly magnetized implant magnet according to an embodiment of the present invention.

FIG. 4 shows an example of an implantable cochlear implant device 400 having an angularly magnetized implant magnet 401 that is encapsulated in a coil housing 402 in which the implant magnet 401 is free to turn around its center cylinder axis of symmetry. On the skin over the cochlear implant device 400 is an external transmitter coil 405 with an external attachment magnet 404, which has a conventional axially-oriented magnetic field. The angular magnetic field of the implant magnet 401 magnetically interacts 403 with the conventional axially-oriented field of the external attachment magnet 404 to hold the external transmitter coil 405 in proper position over the coil housing 402.

Figure 5:
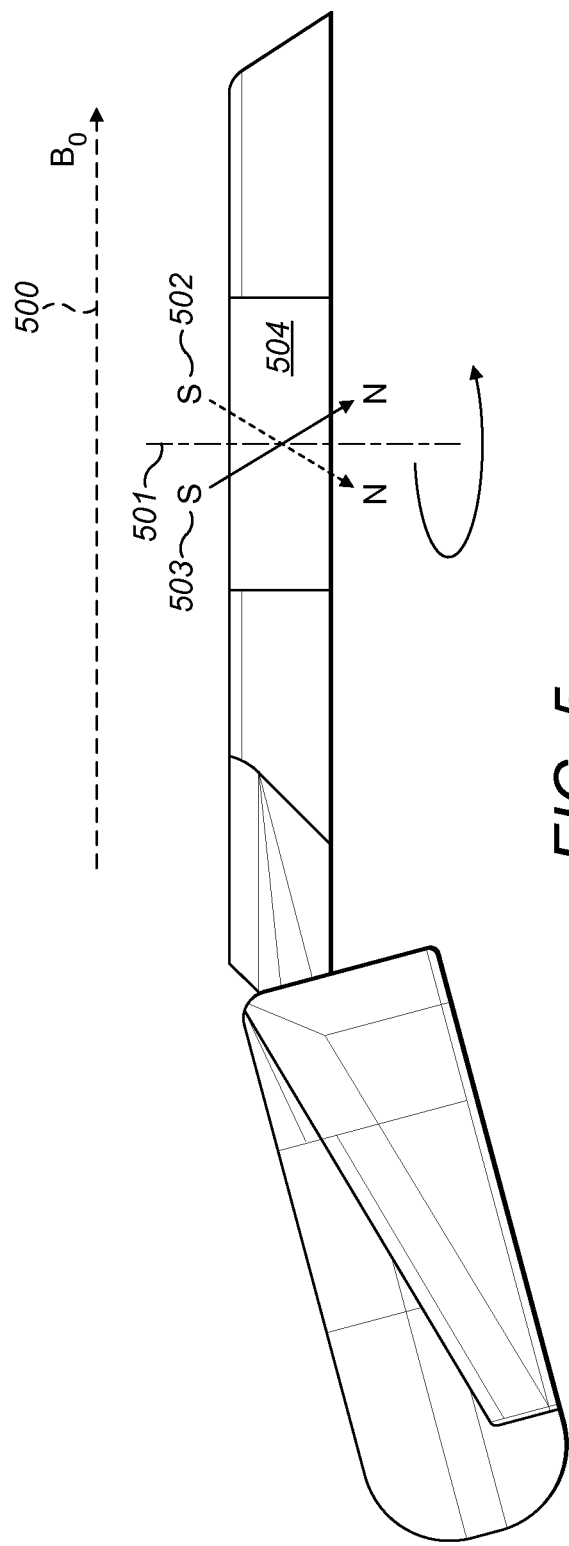
FIG. 5 shows an angularly magnetized implant magnet reaction to an external magnetic field such as from an MRI system.

FIG. 5 shows the reaction of an angularly magnetized implant magnet 504 to an external magnetic field 500. During normal use the implant magnet 504 has some initial angular magnetization direction 502 with respect to the center cylinder axis of symmetry 501 of the implant magnet 504 that allows it to most strongly attract the external attachment magnet (not shown in FIG. 5). When a new strong external magnetic field 500 is imposed—for example, from an MRI procedure—the implant magnet 504 is freely rotatable and will turn around its center cylinder axis of symmetry 501 into a new magnetization direction 503 in which the magnetization of the implant magnet 504 (i.e. magnetic dipole) has a component parallel to the external magnetic field 500 in the MRI scanner.

One significant advantage of an implant magnet with angular magnetization is that when the implant (and magnet) is implanted in a sagittal plane (e.g. a hearing implant), the magnetic field strength of the implant magnet does not weaken if the implanted patient undergoes an MRI procedure, even for high external magnetic field strengths of as great as 3 Tesla. That is because the implant magnet self-aligns with the external magnetic field so that the angle between the magnetization vector (dipole) of the implant magnet and the external magnetic field never exceeds a value of 70° to 80°.

In addition, an implant magnet with angular magnetization is compatible with an external device with conventional axially-magnetized magnet. By contrast, an implant magnet with a magnetization direction that is perpendicular to the geometric axis of the implant magnet (e.g., as in U.S. Patent Publication US20110264172) is not compatible with an external device with an axially-magnetized magnet. A further advantage over a magnet with a magnetization direction perpendicular to its geometric axis is that it does not need significantly greater magnet volume (about 20 to 30% more than a conventional axially magnetized magnet) to achieve the same magnetic attraction between the implant magnet and an external magnet.

However the torque exerted on the implant magnet (and hence to the implant device itself) may be nearly as high as with a conventional axially-magnetized implant magnet; torque is proportional to the sine of the angle between the dipole of the implant magnet and the external magnetic field. In addition, angular magnetization of the implant magnet may allow an external device with a conventional axially-magnetized magnet to attach somewhat eccentrically over the implant device. This may influence the energy supply and data transmission by the communication signal through the intervening skin flap, and the force of magnetic attraction with the external magnet.

Although various exemplary embodiments of the invention have been disclosed, it should be apparent to those skilled in the art that various changes and modifications can be made which will achieve some of the advantages of the invention without departing from the true scope of the invention.

What is claimed is:

1. A magnetic arrangement for an implantable system for a recipient patient, the arrangement comprising:
    an implantable coil housing containing a signal coil for transcutaneous communication of an implant communication signal;
    a cylindrical implant magnet freely rotatable within the coil housing for transcutaneous magnetic interaction with a corresponding external attachment magnet, the implant magnet having:
        i. a central cylinder axis of symmetry, and
        ii. a magnetization direction along a magnetic axis angled away from the axis of symmetry at a non-zero angle less than 45 degrees.

2. An arrangement according to claim 1, wherein the magnetic axis is angled away from the axis of symmetry at an angle of more than 10 degrees.

3. An arrangement according to claim 2, wherein the magnetic axis is angled away from the axis of symmetry at an angle of less than 30 degrees.

4. An arrangement according to claim 1, wherein the magnetic axis is angled away from the axis of symmetry at an angle of 20 degrees.

5. An arrangement according to claim 1, further comprising:
    a lubrication coating covering at least a portion of the implant magnet and reducing rotational friction between the implant magnet and the coil housing.

6. An arrangement according to claim 1, wherein the implantable system is a cochlear implant system.

7. An arrangement according to claim 1, wherein the implantable system is a middle ear implant system.

8. An arrangement according to claim 1, wherein the implantable system is a vestibular implant system.

* * * * *